(12) United States Patent
Remy

(10) Patent No.: US 6,190,677 B1
(45) Date of Patent: Feb. 20, 2001

(54) PROCESS FOR PREPARING A PHOTOCHROMIC COMPOUND AND A COSMETIC COMPOSITION THEREOF

(75) Inventor: Christophe Remy, Paris (FR)

(73) Assignee: L'Oreal

( * ) Notice: Under 35 U.S.C. 154(b), the term of this patent shall be extended for 0 days.

(21) Appl. No.: 09/007,751

(22) Filed: Jan. 15, 1998

(30) Foreign Application Priority Data

Jan. 16, 1997 (FR) .................................................. 97 00413

(51) Int. Cl.$^7$ ................................ A61K 6/00; A61K 7/00; A61K 7/04; A61K 7/025
(52) U.S. Cl. ............................. 424/401; 424/61; 424/64; 424/70.7
(58) Field of Search ................................ 424/61, 401, 450, 424/64, 70.7, 70.1, 59; 514/937, 938, 944, 844, 845

(56) References Cited

U.S. PATENT DOCUMENTS

| | | |
|---|---|---|
| 4,572,618 | 2/1986 | Abraham et al. .................... 350/354 |
| 5,762,915 * | 6/1998 | Saito et al. .............................. 424/59 |
| 5,858,338 * | 1/1999 | Piot et al. ........................... 424/70.7 |
| 5,989,573 * | 6/1998 | Remy .................................. 424/401 |

FOREIGN PATENT DOCUMENTS 0 624 553 * 11/1994 (EP) .

OTHER PUBLICATIONS

Derwent Abstract No. 93–070851 of JP 05–017152.

* cited by examiner

*Primary Examiner*—Thurman K. Page
*Assistant Examiner*—S. Howard
(74) *Attorney, Agent, or Firm*—Finnegan, Henderson, Farabow, Garrett & Dunner, L.L.P.

(57) ABSTRACT

A process for preparing a photochromic compound and/or improving the photochromic properties of a photochromic compound selected from metal oxides, hydrated metal oxides and metal oxide/hydrate complexes by heat-treating the photochromic compound in the presence of at least one metallic component such as an oxide or hydroxide of lithium, sodium and/or potassium, the photochromic compound obtained using this process, and the cosmetic composition comprising it.

40 Claims, No Drawings

PROCESS FOR PREPARING A PHOTOCHROMIC COMPOUND AND A COSMETIC COMPOSITION THEREOF

The present invention relates to the improvement of the photochromic properties of an initially photochromic compound, and to its application in the field of cosmetic compositions, in particular.

Cosmetic compositions, in particular make-up compositions such as free or compact powders, foundations, blushers or eye-shadows, lip compositions or nail varnishes, comprise a suitable vehicle and various colorants intended to impart some degree of color to the compositions before and/or after they are applied to the skin, the mucous membranes, the mucocutaneous tissues and/or parts of the exoskeleton, for example the nails or the hair.

A fairly limited range of colorants is presently used to create colors, in particular lakes, inorganic pigments or pearlescent pigments. Lakes allow vivid colors to be obtained, but are for the most part unstable with respect to light, temperature or pH. Some of them also have the drawback of staining the skin unattractively after they have been applied, as a result of the colorant being leached. Conversely, inorganic pigments, in particular inorganic oxides, are highly stable but give somewhat dull and pale colors. In order to obtain colored effects, use may also be made of pearlescent pigments whose colors are varied, albeit never intense, which make it possible to obtain iridescent but most often fairly weak effects.

It has therefore been proposed to use photochromic compounds in make-up or haircare compositions, so as to obtain attractive and varied changes in the color effect of make-up for the skin and/or the hair.

Photochromic compounds are compounds which have the property of changing color when they are exposed to a light source, then of returning to their initial color, or a similar color, when they are no longer being exposed. In particular, compounds of this type have a particularly advantageous application in cosmetic compositions, in particular in make-up compositions such as foundations and blushers or eye-shadows. Indeed, it has been found that the make-up effect of skin which has been made up differs depending on whether the illumination is natural or artificial. Thus, make-up applied under artificial illumination will appear lighter under natural light. Conversely, make-up applied out of doors will appear darker in a place where the illumination is artificial.

The photochromic properties of a compound can be characterized using two parameters, calculated on the basis of measuring the trichromatic coordinates (L, a and b), in the following way.

A compound which initially has the coordinates (L0, a0, b0) will be considered.

The compound is firstly exposed to a light source for 30 minutes under standard conditions, then the new coordinates (L30, a30 and b30) are measured, these coordinates reflecting the color change due to the exposure. A first parameter $\Delta E30$ can be calculated which reflects the ability of a compound to take on a color different from the original one:

$$\Delta E30 = [(L30-L0)^2 + (a30-a0)^2 + (b30-b0)^2]^{1/2}$$

The compound which has been exposed for 30 minutes is secondly placed in complete darkness for 30 minutes, then the new coordinates (L60, a60 and b60) are measured.

A second parameter $\Delta E60$ can be calculated which reflects the color change with respect to the situation before exposure:

$$\Delta E60 = [(L60-L0)^2 + (a60-a0)^2 + (b60-b0)^2]^{1/2}$$

The value $\Delta(\Delta E)$, equal to the absolute value of the difference between $\Delta E60$ and $\Delta E30$, reflects the capacity of a compound to return, after exposure and darkness, to a color similar to that of the initial state, that is to say before exposure.

The prior art has, in particular, proposed the use in cosmetics of organic photochromic compounds, for example compounds of the spiropyran or naphthoxazine families.

These photochromic compounds are particularly advantageous since they enable the support to which they are applied to change color rapidly when the support is exposed to UV, for example, with rapid return to the initial color when it is no longer being exposed to UV.

Mention may thus be made of French Patent Application FR 1 604 929, which describes cosmetic compositions, in particular for the hair, in aerosol form which contain phototropic compounds such as nitrobenzylpyradines, thiosemicarbazones or spiropyran derivatives. After these compositions have been sprayed onto the hair and exposed to sunlight, a blue-violet coloration is obtained which returns to pale yellow in darkness.

Cosmetic compositions comprising particular inorganic photochromic compounds, selected from metal oxides, their hydrated forms and their complexes, have also been proposed, for example by European Patent Application EP 359 909. In particular, this document mentions the use of titanium oxide, treated so as to make it photochromic, in make-up compositions such as powders and foundations.

Further, U.S. Pat. No. 5,176,905 discloses a process for obtaining a photochromic titanium oxide by mixing iron hydroxide (FeOOH) and titanium dioxide, and calcining at 750–850° C.

In addition, European Patent Application EP 624 553 discloses a process for preparing titanium oxide having improved photochromism, this process involving dissolving an organotitanium compound and an organic compound comprising at least one metal, in an organic solvent, then in hydrolysing the mixture, recovering the hydrolysate and in calcining it at a temperature of 550–700° C. This produces a photochromic titanium oxide having a color difference which can be quantified using the parameter $\Delta E$, the value of which is at least 10. The value $\Delta E$ is the measured difference between the chromaticity before exposure and the chromaticity after exposure for 1 hour, under UV at 2 mW/cm$^2$.

Furthermore, Japanese Patent Application JP 05/017152 discloses a process for preparing a photochromic titanium oxide, involving mixing organotitanium compounds with at least one metal selected from iron, chromium, copper, nickel, vanadium or manganese, then in sintering the mixture in the presence of sodium compounds. It is thus possible to obtain a parameter $\Delta E$ which is improved in comparison with the prior art, and is in particular greater than 10. The parameter $\Delta E$ is calculated in the same way as in EP 624 553.

In the latter two documents, the improved parameter $\Delta E$ reflects the ability of a compound to change color when exposed to light. This document makes absolutely no mention of any improvement of the parameter $\Delta(\Delta E)$, which reflects the ability of the compound to return to a state similar to the initial state.

However, it has been observed that, even though they make it possible to obtain an appreciable change in the color of the make-up, that is to say a relatively large $\Delta E$, the prior art photochromic compounds, in particular the inorganic compounds, nevertheless have the following drawback:

when it is no longer being exposed to light, the color of the make-up does not always return acceptably to its initial color, and in particular does not return completely to a color identical to the initial color. After a cycle of exposure and darkness, the photochromic compound has a color substantially different from its initial color before exposure. The "relaxation of the photochromic compound in the dark" can thus be considered as weak or low. For these compounds, this is characterized by a small value of $\Delta(\Delta E)$, of the order of 3–4.

The object of the present invention is to provide a particular process for improving photochromism, in particular improving the value $\Delta(\Delta E)$ of an initially photochromic compound, while maintaining a satisfactory value $\Delta E30$, that is to say one which is at least of equal value, and often improved, that is to say as high as possible.

The present invention therefore relates to a process for preparing a photochromic compound having a parameter $\Delta(\Delta E)$ greater than or equal to 7, in which a photochromic compound of the metal oxide, hydrated metal oxide or metal oxide and/or hydrate complex type is heat-treated at a temperature ranging from 400 to 1000° C. in the presence of a metallic component selected from the oxides and/or hydroxides of lithium, sodium and/or potassium.

The invention also relates to a process for improving the parameter $\Delta(\Delta E)$ of a photochromic compound of the metal oxide, hydrated metal oxide or metal oxide and/or hydrate complex type, involving heat-treating the compound at a temperature ranging from 400 to 1000° C. in the presence of a metallic component selected from the oxides and/or hydroxides of lithium, sodium and/or potassium.

The invention further relates to the photochromic compound of the metal oxide, hydrated metal oxide or metal oxide and/or hydrate complex type, which can be obtained using one of these processes.

The invention further relates to cosmetic compositions comprising the compound.

Without being limited by the present explanation, the photochromism of a doped titanium oxide may be illustrated as follows. A photochromic titanium oxide of the anatase form will be considered, which is doped with iron atoms of valency 3+ and 4+ substituting for titanium atoms.

When exposed to UV, it can be considered that, by being converted into $Fe^{4+}$, an $Fe^{3+}$ cation will give up an electron to an entity X which will be converted into an entity $X^-$, responsible for the color change of the photochromic compound. X may be considered as an oxygen vacancy in the anatase lattice. It may be assumed that, during a second phase, electrons in the valence band of the titanium oxide will then be moved to the conduction band, consequently generating both free electrons and electron vacancies in the valence band, which are also referred to as positive "holes", i.e., a vacant state in an energy band, corresponding to a region with a negative charge in deficit. It is moreover known that the electrons and the vacancies for the most part tend to recombine. The final phase, the phase of "relaxation in the dark", corresponding to the return to the initial color, takes place through the conversion of $X^-$ to X, with an electron being released to the lattice, for example in a defect of the anionic type associated with an oxygen vacancy, or to an $Fe^{4+}$ formed during the exposure.

The following explanation may be proposed in order to illustrate the mechanism allowing the photochromic properties of a given compound to be improved. A photochromic titanium oxide of the anatase form will be considered, which is doped with iron atoms of valency 3+ and 4+, these being substituted for the titanium of valency 4+ in the anatase crystal lattice. In order to keep the compound electrically neutral, charge compensation must take place, most likely by the creation of oxygen vacancies.

When the process according to the invention is applied, that is to say when the doped titanium oxide is heat-treated in the presence of small ions with weak positive charge, it may be assumed that:

in order to compensate for the addition of positive charge, some of the iron atoms of valency 4+ are converted into iron of valency 3+, releasing an electron for X which is converted into $X^-$. This provides an increase in $\Delta E30$.

in order to compensate for the addition of positive charge, the number of oxygen vacancies and associated anionic defects increases; however, the relaxation in the dark takes place through the release of an electron from $X^-$ to a defect of this type; since the number of these defects is increased by virtue of the process of the invention, the return to the initial color is improved, whence an improved parameter $\Delta(\Delta E)$.

by virtue of the process according to the invention, the iron 3+ in the anatase tends to be preferentially close to an oxygen vacancy; the exchanges of electrons between the iron and the vacancy will therefore be facilitated, whence an increase in the photochromism ($\Delta E30$ and $\Delta(\Delta E)$).

The process according to the invention therefore involves heat-treating a photochromic compound of the metal oxide, hydrated metal oxide or metal oxide and/or hydrate complex type in the presence of a metallic component selected from oxides and/or hydroxides of lithium, sodium and/or potassium.

Among the metal oxides, mention may, in particular, be made of oxides of titanium, niobium, silicon, aluminium, zinc, hafnium, thorium, tin, thallium, zirconium, beryllium, cobalt, calcium and magnesium. The oxides and hydrated oxides of titanium, aluminium, zinc, zirconium, calcium and magnesium are preferred.

More preferably, use will be made of titanium dioxide which can be rendered photochromic using a metal selected from iron, chromium, copper, nickel, manganese, cobalt, molybdenum, as such or in the form of a salt such as a sulphate, a chlorate, a nitrate or an acetate.

The metallic component is preferably selected from the oxides or hydroxides of lithium. Mention may, in particular, be made of lithium hydroxide LiOH, and sodium peroxide $Na_2O_2$.

The metallic component may be present in a concentration preferably ranging from 0.01 to 30% by weight of metal ions, more preferably from 0.02 to 20% by weight, with respect to the weight of photochromic compound to be treated.

The heat-treatment may be carried out at a temperature preferably ranging from 400 to 1000° C., more preferably 600–900° C., for example for a time preferably ranging from 10 minutes to 6 hours, more preferably from 2 to 5 hours.

This produces a heat-treated photochromic compound whose parameter $\Delta(\Delta E)$ is preferably at least equal to 7, more preferably greater than or equal to 10, even more preferably greater than or equal to 12.

The photochromic compound treated according to the process of the invention may be incorporated in a cosmetic composition in a quantity which can be determined easily by the person skilled in the art, on the basis of his general knowledge, and which may, in particular, range from 0.01 to 30% by weight with respect to the total weight of the composition, more preferably 1 to 15% by weight.

The photochromic composition may be in the form of a product to be applied to the mucous membranes, the mucocutaneous tissues and/or the keratinous tissues, such as the skin and parts of the exoskeleton (nails, eyelashes, eyebrows, body hair and head hair). It therefore contains a cosmetically acceptable medium, that is to say a medium which is compatible with all the keratinous materials such as the skin, the nails, the hair, the eyelashes, the eyebrows, the mucous membranes and the mucocutaneous tissues, and any other cutaneous region of the body and the face. The medium may comprise or be in the form of, in particular, a suspension, a dispersion or a solution in solvent or aqueous-alcoholic medium, optionally thickened or gelled; an oil-in-water, water-in-oil or multiple emulsion; a gel or a foam; an emulsified gel; a dispersion of vesicles, in particular lipid vesicles; a two-phase or multi-phase lotion; a spray; a free, compact or loose powder; an anhydrous paste. The person skilled in the art will be able to choose the suitable pharmaceutical form, as well as the method of preparing it, on the basis of general knowledge, while taking into account both the nature of the constituents which are used, in particular their solubility in the support, and the application envisaged for the composition.

When the composition is present in aqueous form, in particular in the form of a dispersion, an emulsion or an aqueous solution, it may comprise an aqueous phase which may comprise water, a floral water such as cornflower water, and/or a mineral water such as water from sources such as Vittel, Vichy, Uriage, Roche Posay, Bourboule, Enghien-les-Bains, Saint Gervais-les-Bains, Néris-les-Bains, Allevar-les-Bains, Digne, Lucas, Maiziéres, Neyrac-les-Bains, Lons-le-Saunier, Eaux Bones, Rochefort, Saint Christau, Fumades and Tercis-les-bains.

The aqueous phase may comprise from 0% to 14% by weight, relative to the total weight of the aqueous phase, of a $C_2$–$C_6$ lower monoalcohol and/or of a polyol such as glycerol, butylene glycol, isoprene glycol, propylene glycol or polyethylene glycol.

When the composition according to the invention is in the form of an emulsion, it may optionally furthermore comprise a surfactant, preferably in an amount of from 0.01 to 30% by weight relative to the total weight of the composition.

Among the anionic surfactants which may be used, alone or as a mixture, mention may in particular be made of alkali metal salts, ammonium salts, amine salts or amino alcohol salts of the following compounds: alkyl sulphates, alkyl ether sulphates, alkylamide sulphates and ether sulphates, alkylarylpolyether sulphates, monoglyceride sulphates, alkylsulphonates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkylsulphosuccinamates, alkyl sulphoacetates, alkyl polyglycerol carboxylates, alkyl phosphates/alkyl ether phosphates, acyl sarcosinates, alkylpolypeptidates, alkylamidopolypeptidates, acyl isenthionates, alkyl laurates. The alkyl or acyl radical in all of these compounds generally denotes a chain of 12 to 18 carbon atoms. Mention may also be made of soaps and fatty acid salts such as oleic acid, ricinoleic acid, palmitic acid, stearic acid, coconut oil acid or hydrogenated coconut oil acid and, in particular, amine salts such as amine stearates; acyl lactylates in which the acyl radical comprises 8–20 carbon atoms; carboxylic acids of polyglycol ethers corresponding to the formula:

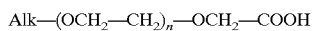

in acid or salified form, in which the substituent Alk corresponds to a straight chain having from 12 to 18 carbon atoms, and in which n is an integer ranging from 5 to 15.

Among the non-ionic surfactants which may be used, alone or as a mixture, mention may in particular be made of: polyethoxylated, polypropoxylated or polyglycerolated fatty acids, alkylphenols and alcohols which have a fatty chain containing from 8 to 18 carbon atoms; copolymers of ethylene oxide and of propylene oxide, condensates of ethylene oxide and of propylene oxide with fatty alcohols, polyethoxylated fatty amides, polyethoxylated fatty amines, ethanolamides, fatty acid esters of glycol, fatty acid esters of oxyethylenated or non-oxyethylenated sorbitan, fatty acid esters of saccharose, fatty acid esters of polyethylene glycol, phosphoric triesters, fatty acid esters of glucose derivatives; alkyl polyglycosides and alkylamides of amino sugars; condensation products of an α-diol, of a monoalcohol, of an alkylphenol, of an amide or of a diglycolamide with glycidol or a glycidol precursor.

The composition according to the invention may also comprise preferably from 0 to 5% by weight, relative to the total weight of the emulsion, of at least one co-emulsifier which may be selected from oxyethylenated sorbitan monostearate, fatty alcohols such as stearyl alcohol or cetyl alcohol, or fatty acid esters of polyols such as glyceryl stearate.

The composition according to the invention may furthermore comprise one or more thickeners in preferred concentrations ranging from 0 to 6% by weight, relative to the total weight of the composition, which are selected from:

polysaccharide biopolymers such as xanthan gum, carob gum, guar gum, alginates, modified celluloses such as hydroxyethylcellulose, methylcellulose, hydroxypropylcellulose and carboxymethylcellulose, starch derivatives, cellulose ether derivatives containing quaternary ammonium groups, cationic polysaccharides;

synthetic polymers, for instance polyacrylic acids such as polyglyceryl (meth)acrylate polymers such as HISPAGEL or LUBRAGEL from the companies Hispano Quimica or Gardian, polyvinylpyrrolidone, polyvinyl alcohol, crosslinked polymers of acrylamide and of ammonium acrylate such as PAS 5161 or BOZEPOL C from Hoechst; acrylate/octylacrylamide copolymers such as DERMACRYL from National Starch; polyacrylamide-based polymers such as SEPIGEL 305 from Seppic, crosslinked polymers of acrylamide and of methacryloyloxyethyltrimethylammonium chloride, such as SALCARE SC 92 from Allied Colloids, magnesium aluminium silicate.

Depending on the application envisaged, the composition may furthermore comprise a film-forming polymer. This is, in particular, the case when it is desired to prepare a composition of the nail varnish, mascara or eye-liner type or a haircare composition of the lacquer type. The polymers may be dissolved or dispersed in the cosmetically acceptable medium. In particular, the polymer may be present in the form of a solution in an organic solvent or in the form of an aqueous dispersion of film-forming polymer particles. The polymer may be selected from nitrocellulose, cellulose acetobutyrate, polyvinyl butyrals, alkyd resins, polyesters, acrylics, vinyls and/or polyurethanes. Mention may, in particular, be made of the copolymers of (meth)acrylic acid and of at least one ester monomer of linear, branched or cyclic (meth)acrylic acid and/or of at least one amide monomer of linear, branched or cyclic, mono- or disubstituted (meth)acrylic acid; (meth)acrylic acid/tert-butyl (meth)acrylate and/or isobutyl (meth)acrylate/$C_1$–$C_4$ alkyl (meth)acrylate copolymers; (meth)acrylic acid/ethyl acrylate/methyl methacrylate terpolymers and tetrapolymers; methyl methacrylate/butyl or ethyl acrylate/ hydroxyethyl or 2-hydroxypropyl acrylate or methacrylate/(meth)acrylic acid tetrapolymers; copolymers of acrylic acid and of $C_1$–$C_4$ alkyl methacrylate; terpolymers of vinylpyrrolidone, of acrylic acid and of $C_{1-20}$ alkyl methacrylate; amphoteric copolymers; vinyl esters of branched acids; vinyl esters of benzoic acid; copolymers of (meth) acrylic acid and of at least one olefinic monomer; copolymers of vinyl monoacid and/or of allylic monoacid. Among the resins, mention may be made of resins of the arylsulphonamide formaldehyde or arylsulphonamide epoxy type; resins of the acrylic, styrene, styreneacrylate and vinylacrylate type.

The composition may also comprise at least one plasticizer, such as tricresyl phosphate, benzyl benzoate, triethyl citrate, tributyl citrate, triethyl acetyl citrate, 2-triethylhexyl acetyl citrate, camphor; glycol ethers; castor oil oxyethylenated with 40 mol of ethylene oxide; propylene glycol; butyl glycol; ethylene glycol monomethyl ether acetate; propylene glycol ethers; ester ethers of propylene glycol and ethylene glycol; esters of diacids such as diethyl, dibutyl and diisopropyl phthalates and adipates, diethyl and dibutyl tartrates, diethyl and dibutyl succinates, diethyl and dibutyl sebacates, diethyl, dibutyl and 2-diethylhexyl phosphates, diethyl or dibutyl acetyl citrate; glycerol esters. The plasticizers may generally be present in a concentration ranging from 1% to 40% by weight relative to the total weight of the composition.

The composition according to the invention may also comprise a fatty phase, in particular including fatty substances which are liquid at 25° C., such as oils of animal, vegetable, mineral or synthetic origin; fatty substances which are solid at 25° C., such as waxes of animal, vegetable, mineral or synthetic origin; fatty substances in paste form; gums; mixtures thereof.

The compositions according to the invention may thus comprise volatile oils, which evaporate on contact with the skin but whose presence in the cosmetic composition is useful since they make it easier to spread the composition when it is applied to the skin. Spreading agents of this type, referred to here as "volatile oils" are generally oils which, at 25° C., have a saturated vapour pressure at least equal to 0.5 millibar (i.e. 50 Pa). Use is preferably made of oils whose flashpoint is high enough to allow these oils to be used in formulation, and low enough to obtain the desired evanescent effect. Oils whose flashpoint is of the order of 40–100° C. are preferably employed.

Mention may thus be made of volatile silicone oils, such as:
cyclic volatile silicones having 3 to 8, and preferably 4 to 6, silicon atoms. Examples of these include cyclotetradimethylsiloxane, cyclopentadimethylsiloxane or cyclohexadimethylsiloxane,
cyclocopolymers of the dimethylsiloxane/methylalkylsiloxane type, such as SILICONE FZ 3109 marketed by the company Union Carbide, which is a dimethylsiloxane/methyloctylsiloxane cyclocopolymer,
linear volatile silicones having 2 to 9 silicon atoms. Examples of these include hexamethyidisiloxane, hexylheptamethyltrisiloxane or octylheptamethyltrisiloxane.

Mention may also be made of volatile hydrocarbon oils such as isoparaffins and, in particular, isododecane; and fluorinated oils such as the one marketed under the name GALDEN® (Montefluos).

Use may also be made of non-volatile oils, among which mention may be made of:

poly($C_1$–$C_{20}$)alkylsiloxanes and, in particular those having trimethylsilyl end groups, preferably those whose viscosity is less than 0.06 m$^2$/s, among which mention may be made of linear polydimethylsiloxanes and alkylmethylpolysiloxanes such as cetyidimethicone (CTFA name), silicones modified with aliphatic and/or aromatic groups, which may or may not contain fluorine, or with functional groups such as hydroxyl, thiol, and/or amine groups, phenylated silicone oils, in particular those of formula:

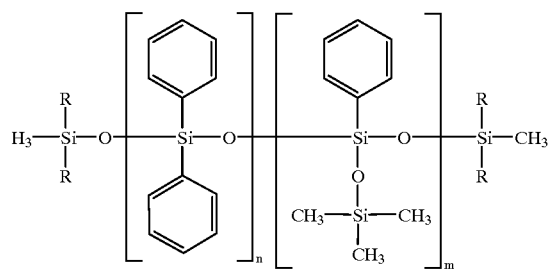

in which
R independently denotes a $C_1$–$C_{30}$ alkyl radical, an aryl radical or an aralkyl radical, n is an integer ranging from 0 to 100, and
m is an integer ranging from 0 to 100, with the condition that the sum of n+m ranges from 1 to 100, oils of animal, vegetable or mineral origin, and in particular animal or vegetable oils formed by fatty acid esters of polyols, in particular liquid triglycerides, for example sunflower oil, corn oil, soy bean oil, marrow oil, grapeseed oil, sesame oil, hazelnut oil, apricot oil, almond oil or avocado oil; fish oils, glyceryl tricaprocaprylate, or vegetable or animal oils of formula $R_1COOR_2$ in which $R_1$ represents a higher fatty acid residue containing from 7 to 19 carbon atoms and $R_2$ represents a branched hydrocarbon chain containing from 3 to 20 carbon atoms, for example Purcellin oil; liquid paraffin, liquid petroleum jelly, perhydrosqualene, wheatgerm oil, beauty-leaf oil, sesame oil, macadamia oil, grapeseed oil, colza oil, copra oil, arachis oil, palm oil, castor oil, jojoba oil, olive oil or cereal germ oil; fatty acid esters, alcohols; acetylglycerides; octanoates, decanoates or ricinoleates of alcohols or of polyalcohols; fatty acid triglycerides, glycerides;

fluorinated and perfluorinated oils.

The composition according to the invention may furthermore comprise other fatty substances, which may be selected by the person skilled in the art on the basis of general knowledge, so as to give the final composition the desired properties, for example in terms of consistency and/or texture. These additional fatty substances may be waxes, gums and/or fatty substances in paste form of animal, vegetable, mineral or synthetic origin, as well as mixtures thereof.

Mention may, in particular, be made of:
silicone gums,
waxes of animal, vegetable, mineral or synthetic origin, such as microcrystalline waxes, paraffin, petrolatum, petroleum jelly, ozokerites, montan wax; beeswax, lanolin and derivatives thereof; candellila wax, ouricurry wax, carnauba wax, Japan wax, cocoa butter, cork fibre wax or sugarcane wax; hydrogenated oils which are solid at 25° C., ozokerites, fatty esters and glycerides which are solid at 25° C.; polyethylene waxes and waxes obtained by Fischer-Tropsch synthesis; hydrogenated oils which are solid at 25° C.; lanolins; fatty esters which are solid at 25° C.; silicone waxes; fluorinated waxes.

The composition according to the invention may also comprise one or more organic solvents which are cosmetically acceptable (acceptable in terms of tolerance, toxicology and feel). These organic solvents may represent from 0% to 98% of the total weight of the composition and may be selected from hydrophilic organic solvents, lipophilic organic solvents, amphiphilic solvents or mixtures thereof.

Among the hydrophilic organic solvents, mention may, for example, be made of linear or branched lower monoalcohols having from 1 to 8 carbon atoms, such as ethanol, propanol, butanol, isopropanol, isobutanol; polyethylene glycols having from 6 to 80 ethylene oxides; polyols such as propylene glycol, isoprene glycol, butylene glycol, glycerol and sorbitol; mono- or dialkyl isosorbide in which the alkyl groups have from 1 to 5 carbon atoms; glycol ethers such as diethylene glycol monomethyl or monoethyl ether and propylene glycol ethers such as dipropylene glycol methyl ether. As amphiphilic organic solvents, mention may be made of polyols such as polypropylene glycol (PPG) derivatives such as fatty acid esters of polypropylene glycol and fatty alcohol esters of PPG for example PPG-23 oleyl ether and PPG-36 oleate. As lipophilic organic solvents, mention may, for example, be made of fatty esters such as diisopropyl adipates, dioctyl adipates, alkyl benzoates, isopropyl myristate, isopropyl palmitate, butyl stearate, hexyl laurate, isononyl isononanoate, 2-ethylhexyl palmitate, 2-hexydecyl laurate, 2-octyidecyl palmitate, 2-octyldecyl myristate, bis (2-hexylethyl) succinate, diisostearyl malate, 2-octyldodecyl lactate, glyceryl triisostearate and diglyceryl triisostearate.

The composition may furthermore comprise a particulate phase, which may comprise pigments and/or pearlescent agents and/or fillers customarily used in cosmetic compositions. The term pigments should be understood to mean white or colored, inorganic or organic particles intended to color and/or opacify the composition. The term fillers should be understood to mean colorless or white, inorganic or synthetic, lamellar or non-lamellar particles intended to give the composition body or rigidity, and/or softness, a mafte effect and uniformity when applied as make-up. The term pearlescent agents should be understood to mean iridescent particles which reflect light.

The pigments may be present in the composition at a level preferably ranging from 0 to 15% by weight of the final composition, more preferably from 8 to 10% by weight. They may be white or colored, inorganic and/or organic, and of customary or nanometric size. Mention may be made of titanium, zirconium or cerium dioxides, as well as zinc oxide, iron oxide or chromium oxide, ferric blue, chromium hydrate, carbon black, ultramarines (aluminosilicate polysulphides), manganese pyrophosphate and certain metal powders such as those of silver or of aluminium, and carbon black. Mention may also be made of the lakes commonly used to give a make-up effect to the lips and the skin, these lakes being salts of calcium, barium, aluminium or zirconium, or acidic colorants such as, for example, haloacid, azo, and anthraquinone dyes.

The pearlescent agents may be present in the composition at a concentration preferably ranging from 0 to 20% by weight, more preferably from 8 to 15% by weight. Examples of the pearlescent agents which may be envisaged include natural mother-of-pearl, mica coated with titanium oxide, with iron oxide, with natural pigment or with bismuth oxychioride, as well as colored titanium mica.

The fillers, which may be present at a concentration preferably ranging from 0 to 30% by weight, more preferably 5 to 15%, in the composition, may be inorganic or synthetic, lamellar, or non-lamellar. Mention may be made of talc, mica, silica, kaolin, nylon powders and polyethylene powders, Teflon, starch, boron nitride, polymer microspheres such as EXPANCEL (Nobel Industrie), polytrap (Dow Corning) and silicone resin microbeads (TOSPEARLS from Toshiba for example), precipitated calcium carbonate, magnesium carbonate or hydrocarbonate, metal soaps derived from organic carboxylic acids having from 8 to 22 carbon atoms.

Depending on the type of formulation, the pulverulent phase may represent from 0.01 to 99% by weight of the composition.

The composition may furthermore comprise a colorant, in particular a natural organic colorant such as cochineal carmine, and/or a synthetic colorant such as haloacid, azo or anthraquinone dyes. Mention may also be made of inorganic colorants such as copper sulphate.

The composition may furthermore comprise any additive customarily used in the field of cosmetics, for example antioxidants, fragrances, essential oils, preserving agents, lipophilic or hydrophilic cosmetic active agents, moisturizers, vitamins, essential fatty acids, sphingolipids, self-tanning agents such as DHA, sunscreens, anti-foaming agents, sequestering agents and antioxidants.

Clearly, the person skilled in the art will take care to select the optional additional compounds, and/or their amount, so that the advantageous properties of the composition according to the invention are not, or are not substantially, adversely affected by the addition which is envisaged.

The cosmetic compositions may be in the form of a care and/or make-up product for the skin, a suncare or self-tanning product, or a haircare product. In particular, they find a particular application in the field of lip compositions, foundations, blushers or eye-shadows, loose or compact powders, tinted creams, eye-liners, mascaras and aqueous or solvent-based nail varnishes.

The invention is illustrated, but in no way limited, by the following examples.

EXAMPLE 1

The photochromic compound taken as an example was iron-doped titanium oxide marketed by C.C.I.C. through IKEDA under the name "PHOTOGENICA 1".

Its initial characteristics were as follows:
after 30 minutes of exposure to a lamp emitting at 365 nm:
$\Delta E30=12.0$ after 30 minutes of darkness: $\Delta(\Delta E)=4.2$ a/Heat-treatment in the Presence of LIOH A mixture was prepared comprising iron-doped titanium oxide and 0.9% by weight of LiOH, corresponding to 0.25% by mass of $Li^+$. The mixture was mechanically mixed in a mortar, then heat-treated for 4 hours in a tube furnace at a temperature of about 800° C.

The results given in the following table were obtained.

b/Heat-treatment in the Presence of $Na_2O_2$

A mixture was prepared comprising iron-doped titanium oxide and 30% by weight of $Na_2O_2$, corresponding to 18% by mass of Na+. The mixture was mechanically mixed in a mortar, then heat-treated for 4 hours in a tube furnace at a temperature of about 800° C. The results given in the following table were obtained.

|  | ΔE30 | Δ(ΔE) |
|---|---|---|
| Iron-doped titanium oxide | 12.0 | 4.2 |
| After treatment with LiOH | 17.0 | 12.0 |
| After treatment with Na$_2$O$_2$ | 12.3 | 7.6 |

The process according to the invention therefore allows the value of Δ(ΔE) to be improved while maintaining an acceptable, or even improved, value of ΔE30.

EXAMPLE 2

The following were added to pure titanium oxide of the anatase type, dispersed in 50 ml of water:
Composition 1:—0.41% of iron in the form of FeCl$_3$ (% calculated as Fe$_2$O$_3$ mass equivalent relative to titanium oxide), and
Composition 2:—0.41% of iron in the form of FeCl$_3$ (% calculated as Fe$_2$O$_3$ mass equivalent relative to titanium oxide), and—0.05% of lithium, in the form of LiOH (by mass of Li$_+$ relative to the titanium oxide).

The mixtures were evaporated at room temperature while being stirred, so as to distribute the iron and lithium+iron ions uniformly, then the powder obtained was heat-treated for 4 hours in a tube furnace at a temperature of about 800° C.

The results given in the following table were obtained.

|  | ΔE30 | Δ(ΔE) |
|---|---|---|
| Composition 1: With 0.41% of iron | 10 | 5 |
| Composition 2: With 0.41% of iron + 0.05% of lithium | 22.6 | 17.2 |

It is therefore seen that the treatment according to the process of the invention makes it possible to obtain photochromic properties which are better than those obtained according to the prior art.

EXAMPLE 3

A compact powder having the following composition is prepared:

| talc | 30 g |
|---|---|
| mica | 20 g |
| BiOCl | 10 g |
| nylon powder | 16 g |
| zinc stearate | 5 g |
| iron oxide | 2 g |
| titanium oxide according to Example 1a) | 10 g |
| fatty binder | 7 g |

A composition having good cosmetic properties is obtained.

I claim:

1. A process for preparing a photochromic compound having a parameter Δ(ΔE) of at least 7, comprising heat-treating at least one photochromic compound selected from metal oxides, hydrated metal oxides and metal oxide/hydrate complexes at a temperature ranging from 400 to 1000° C. in the presence of at least one metallic component selected from oxides and hydroxides of lithium, sodium and potassium.

2. A process according to claim 1, wherein said at least one photochromic compound is selected from oxides and hydrated oxides of titanium, niobium, silicon, aluminium, zinc, hafnium, thorium, tin, thallium, zirconium, beryllium, cobalt, calcium and magnesium.

3. A process according to claim 1, wherein said at least one photochromic compound is titanium dioxide rendered photochromic by a metal selected from iron, chromium, copper, nickel, manganese, cobalt, molybdenum, and salts thereof.

4. A process according to claim 3, wherein said salts are selected from sulphates, chlorates, nitrates and acetates.

5. A process according to claim 1, wherein said at least one metallic component is selected from oxides and hydroxides of lithium.

6. A process according to claim 1, wherein said at least one metallic component is present in a concentration ranging from 0.01 to 30% by weight of metal ions with respect to the total weight of said photochromic compound.

7. A process according to claim 6, wherein said at least one metallic component is present in a concentration ranging from 0.02 to 20% by weight of metal ions with respect to the total weight of said photochromic compound.

8. A process according to claim 1, wherein said heat treating is carried out at a temperature ranging from 600 to 900° C.

9. A process according to claim 1, wherein said heat treating is carried out for a time ranging from 10 minutes to 6 hours.

10. A process according to claim 9, wherein said heat treating is carried out for a time ranging from 2 to 5 hours.

11. A photochromic compound obtained according to claim 1.

12. A photochromic compound according to claim 11, wherein said parameter Δ(ΔE) is at least 10.

13. A photochromic compound according to claim 12, wherein said parameter Δ(ΔE) is at least 12.

14. A cosmetic composition comprising at least one compound according to claim 11.

15. A cosmetic composition according to claim 14, wherein said at least one compound is present in a concentration ranging from 0.01 to 30% by weight, relative to the total weight of said cosmetic composition.

16. A cosmetic composition according to claim 15, wherein said at least one compound is present in a concentration ranging from 1 to 15% by weight, relative to the total weight of said cosmetic composition.

17. A cosmetic composition according to claim 14, wherein said cosmetic composition is in the form of an optionally thickened or gelled suspension, dispersion or solution in solvent or aqueous-alcoholic medium; an oil-in-water, water-in-oil or multiple emulsion; a gel or a foam; an emulsified gel; a dispersion of vesicles; a two-phase or multi-phase lotion; a spray; a free, compact or loose powder; or an anhydrous paste.

18. A cosmetic composition according to claim 17, wherein said vesicles are lipid vesicles.

19. A cosmetic composition according to claim 14, wherein said cosmetic composition is in the form of a care and/or make-up product for the skin; a suncare or self-tanning product; or a haircare product.

20. A cosmetic composition according to claim 19, wherein said make-up product is in the form of a lip composition, a foundation, a blusher or eye-shadow, a free or compact powder, a tinted cream, an eye-liner, a mascara, or a nail varnish.

21. A process for improving the parameter $\Delta(\Delta E)$ of at least one photochromic compound selected from metal oxides, hydrated metal oxides and metal oxide/hydrate complexes, said process comprising heat-treating, for the purpose of improving said parameter $\Delta(\Delta E)$, said at least one photochromic compound at a temperature ranging from 400 to 1000° C. in the presence of at least one metallic component selected from oxides and hydroxides of lithium, sodium and potassium.

22. A process according to claim 21, wherein said at least one photochromic compound is selected from oxides and hydrated oxides of titanium, niobium, silicon, aluminium, zinc, hafnium, thorium, tin, thallium, zirconium, beryllium, cobalt, calcium and magnesium.

23. A process according to claim 22, wherein said at least one photochromic compound is titanium dioxide rendered photochromic by a metal selected from iron, chromium, copper, nickel, manganese, cobalt, molybdenum, and salts thereof.

24. A process according to claim 23, wherein said salts are selected from sulphates, chlorates, nitrates and acetates.

25. A process according to claim 21, wherein said at least one metallic component is selected from oxides and hydroxides of lithium.

26. A process according to claim 21, wherein said at least one metallic component is present in a concentration ranging from 0.01 to 30% by weight of metal ions with respect to the total weight of said photochromic compound.

27. A process according to claim 26, wherein said at least one metallic component is present in a concentration ranging from 0.02 to 20% by weight of metal ions with respect to the total weight of said photochromic compound.

28. A process according to claim 21, wherein said heat treating is carried out at a temperature ranging from 600 to 900° C.

29. A process according to claim 21, wherein said heat treating is carried out for a time ranging from 10 minutes to 6 hours.

30. A process according to claim 29, wherein said heat treating is carried out for a time ranging from 2 to 5 hours.

31. A photochromic compound obtained according to claim 21.

32. A photochromic compound according to claim 31, wherein said parameter $\Delta(\Delta E)$ is at least 10.

33. A photochromic compound according to claim 32, wherein said parameter $\Delta(\Delta E)$ is at least 12.

34. A cosmetic composition comprising at least one compound according to claim 31.

35. A cosmetic composition according to claim 34, wherein said at least one compound is present in a concentration ranging from 0.01 to 30% by weight, relative to the total weight of said cosmetic composition.

36. A cosmetic composition according to claim 35, wherein said at least one compound is present in a concentration ranging from 1 to 15% by weight, relative to the total weight of said cosmetic composition.

37. A cosmetic composition according to claim 34, wherein said cosmetic composition is in the form of an optionally thickened or gelled suspension, dispersion or solution in solvent or aqueous-alcoholic medium; an oil-in-water, water-in-oil or multiple emulsion; a gel or a foam; an emulsified gel; a dispersion of vesicles; a two-phase or multi-phase lotion; a spray; a free, compact or loose powder; or an anhydrous paste.

38. A cosmetic composition according to claim 37, wherein said vesicles are lipid vesicles.

39. A cosmetic composition according to claim 34, wherein said cosmetic composition is in the form of a care and/or make-up product for the skin; a suncare or self-tanning product; or a haircare product.

40. A cosmetic composition according to claim 39, wherein said make-up product is in the form of a lip composition, a foundation, a blusher or eye-shadow, a free or compact powder, a tinted cream, an eye-liner, a mascara, or a nail varnish.

* * * * *